United States Patent
Awbrey et al.

(10) Patent No.: US 8,519,180 B2
(45) Date of Patent: *Aug. 27, 2013

(54) SYSTEMS AND METHODS FOR PROCESSING GLYCEROL

(75) Inventors: Spencer S. Awbrey, Conroe, TX (US); John Deloach, Daisetta, TX (US); Tony Alexander, Daisetta, TX (US); Don Darbonne, Liberty, TX (US); Marilyn Darbonne, legal representative, Liberty, TX (US)

(73) Assignee: Envirosource, Inc., Liberty, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/589,607

(22) Filed: Aug. 20, 2012

(65) Prior Publication Data

US 2012/0317875 A1    Dec. 20, 2012

Related U.S. Application Data

(63) Continuation of application No. 13/078,479, filed on Apr. 1, 2011, now Pat. No. 8,247,600.

(60) Provisional application No. 61/320,408, filed on Apr. 2, 2010.

(51) Int. Cl.
*C10L 1/19* (2006.01)
*C01G 33/00* (2006.01)

(52) U.S. Cl.
USPC ............................................. 562/23; 562/8

(58) Field of Classification Search
None
See application file for complete search history.

(56) References Cited

U.S. PATENT DOCUMENTS 8,247,600 B2 * 8/2012 Awbrey et al. ............... 562/23

* cited by examiner

*Primary Examiner* — Yevegeny Valenrod
(74) *Attorney, Agent, or Firm* — Edmonds & Nolte, P.C.

(57) ABSTRACT

Systems and methods for processing glycerol into one or more products are provided. In at least one specific embodiment, the method can include decreasing a pH of a mixture comprising glycerol and fatty acids to produce an emulsion comprising a glycerol-rich portion and a fatty acids-rich portion. At least a portion of the glycerol-rich portion can be reacted with an acid comprising phosphorus at conditions sufficient to produce a reacted product comprising glycerophosphoric acid, glycerol, and a portion of the acid.

32 Claims, 1 Drawing Sheet

SYSTEMS AND METHODS FOR PROCESSING GLYCEROL

CROSS REFERENCE TO RELATED APPLICATION

This application is a continuation of co-pending U.S. patent application having Ser. No. 13/078,479, filed on Apr. 1, 2011, and published as U.S. Publication No. 2011/0179696, which claims the benefit of U.S. Provisional Patent Application having Ser. No. 61/320,408, filed on Apr. 2, 2010, which are both incorporated by reference herein.

BACKGROUND

1. Field

Embodiments described herein generally relate to systems and methods for processing a glycerol-containing feed. More particularly, such embodiments relate to systems and methods for processing a glycerol-containing feed into one or more products.

2. Description of the Related Art

The level of biodiesel production, an alternative fuel source, has increased significantly in recent years. A byproduct derived from the biodiesel manufacturing process is glycerol, often referred to as "waste glycerol," "crude glycerol," or "raw glycerol." For every tonne (metric ton) of biodiesel made from vegetable oil, about 100 kg of thick viscous glycerol is produced as a byproduct. Europe alone produces around 6.8 billion liters of biodiesel, which generates around 680,000 tonnes of waste glycerol every year. And the recent and rapid expansion in biodiesel production has resulted in a global oversupply of waste glycerol.

Although some of the waste glycerol is purified for pharmaceutical or food applications, the majority ends up as waste. Waste glycerol is typically incinerated, which is a less than optimal use for a low cost and readily available byproduct.

There is a need, therefore, for new systems and methods for processing glycerol into one or more products.

SUMMARY

Systems and methods for processing glycerol into one or more products are provided. In at least one specific embodiment, the method can include decreasing a pH of a mixture comprising glycerol and fatty acids to produce an emulsion comprising a glycerol-rich portion and a fatty acids-rich portion. At least a portion of the glycerol-rich portion can be reacted with an acid comprising phosphorus at conditions sufficient to produce a reacted product comprising glycerophosphoric acid, glycerol, and a portion of the acid.

In at least one other specific embodiment, the method can include decreasing a pH of a biodiesel byproduct comprising fatty acids, glycerol, water, methanol, and one or more inorganic salts to produce an emulsion comprising a glycerol-rich portion and a fatty acids-rich portion. At least a portion of any methanol contained in the glycerol-rich portion can be removed to produce a methanol-lean glycerol-rich portion. At least a portion of the methanol-lean glycerol-rich portion can be reacted with a first acid comprising phosphorus at conditions sufficient to produce a reacted product comprising glycerophosphoric acid, glycerol, and a portion of the acid.

In at least one other specific embodiment, the method can include mixing a biodiesel byproduct with a sufficient amount of a first acid comprising phosphorus to produce a mixture having a pH of less than about 5.5. The biodiesel byproduct can include fatty acids, glycerol, water, methanol, one or more inorganic salts, and water. The mixture can be allowed to separate into a glycerol-rich portion and a fatty acids-rich portion. The glycerol-rich portion can be recovered. At least a portion of any methanol contained in the glycerol-rich portion can be removed to produce a methanol-lean glycerol-rich portion. At least a portion of the methanol-lean glycerol-rich portion can be reacted with a second acid comprising phosphorus at conditions sufficient to produce a reacted product comprising glycerophosphoric acid, glycerol, water, and a portion of the first acid, a portion of the second acid, or both.

DETAILED DESCRIPTION

Figure 1:
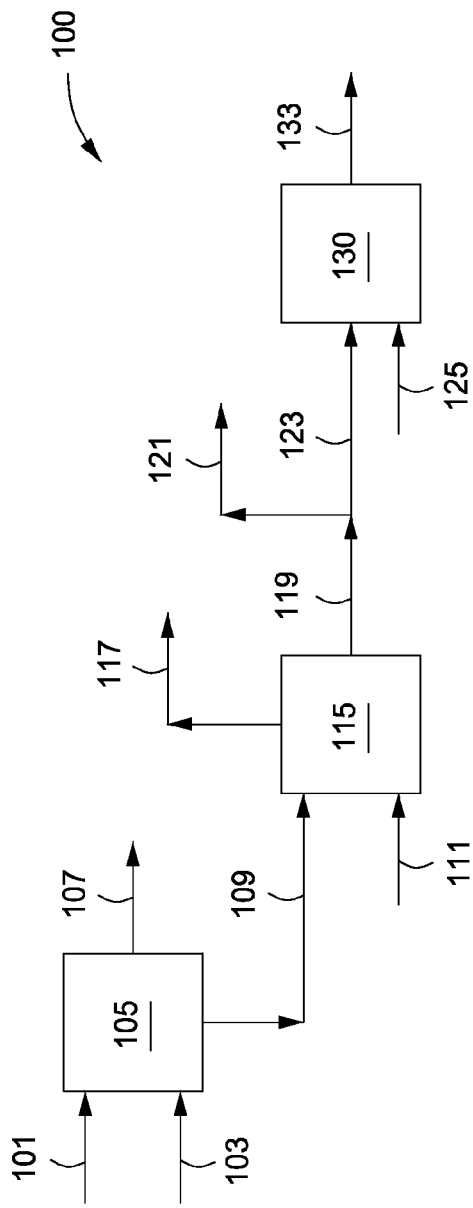
FIG. 1 depicts an illustrative system for processing glycerol, according to one or more embodiments described.

FIG. 1 depicts an illustrative system 100 for processing glycerol, according to one or more embodiments. A glycerol-containing feed via line 101 and an acid via line 103 can be introduced to one or more mixers 105, where the two components can be mixed, blended, contacted, or otherwise combined together to produce a mixture. The mixture can be allowed to separate within the mixer 105 into two or more fractions or portions, including a first portion or glycerol-lean portion and a second portion or glycerol-rich portion.

As used herein, the terms "glycerol-lean portion" and "fatty acids-rich portion" are used interchangeably to refer to a mixture or composition that has a greater concentration of fatty acids than glycerol. Similarly, the term "glycerol-rich portion" and "fatty acids-lean portion" are used interchangeably to refer to a mixture or composition that has a greater concentration of glycerol than fatty acids.

The mixture can be heated to accelerate the separation of the mixture into the two or more fractions or portions. For example, the mixture can be heated to a temperature ranging from a low of about 25° C., about 28° C., or about 30° C. to a high of about 35° C., about 38° C., or about 41° C.

The glycerol-containing feed in line 101 can include, but is not limited to, glycerol, monoglycerides, diglycerides, methanol, soaps of fatty acids, fatty acids, organic salts, inorganic salts, water, biodiesel, solids, or any combination thereof. The glycerol-containing feed in line 101 can come from any source, process, or any number of sources and/or processes. For example, the glycerol-containing feed in line 101 can be or include a byproduct from the production of biodiesel. In another example, the glycerol-containing feed can be or include a byproduct from the production of soaps, e.g., produced by the saponification of animal fats. In yet another example, the glycerol-containing feed in line 101 can include glycerol produced from the conversion of epichlorohydrin. In yet another example, the glycerol-containing feed in line 101 can be or include a byproduct from the refining of cooking and salad oils. In yet another example, the glycerol containing feed can be or include technical or USP Grade glycerol.

Depending, at least in part, on the source of origin, the glycerol-containing feed in line 101 can have a pH ranging from a low of about 6, about 6.5, or about 7 to a high of about 9, about 11, or about 13. The glycerol-containing feed in line 101 can have a glycerol concentration ranging from about 1 wt % to about 99 wt %. The particular make-up or composition of the glycerol-containing feed in line 101 can widely vary. For example, in addition to the glycerol, the glycerol-containing feed in line 101 can also include from about 5 wt % to about 35 wt % methanol, from about 5 wt % to about 25 wt % water, from about 20 wt % to about 55 wt % fatty acids and/or soaps of fatty acids, from about 0.5 wt % to about 10 wt % inorganic and/or organic salts. The fatty acids can include acyclic and/or aliphatic carboxylic acids. Such fatty acids can contain any where from 8 to 22 carbon atoms. With respect to carbon-carbon bonds, the fatty acids can be saturated, monounsaturated, or polyunsaturated. The organic salts can include, but are not limited to, sodium, lithium, salts of fatty acids, proteins, or any combination thereof. The inorganic salts can include, but are not limited to, sodium chloride (NaCl), potassium chloride (KCl), lithium chloride (LiCl), or any combination thereof. The solids can include, but are not limited to, fats, carbons, salts of fatty acids, polymers of fatty acids, or any combination thereof The acid in line 103 can be or include one or more phosphorus-containing acids. For example, the acid in line 103 can be or include one or more phosphoric acids, derivatives thereof, or any combination thereof. Illustrative phosphoric acids can include, but are not limited to, orthophosphoric acid ($H_3PO_4$), polyphosphoric acids such as pyrophosphoric acid ($H_4P_2O_7$), tripolyphosphoric acid ($H_5P_3O_{10}$), and tetrapolyphosphoric acid ($H_6P_4O_{13}$), metaphosphoric acids such as trimetaphosphoric acid ($H_3P_3O_9$) and tetrametaphosphoric acid ($H_4P_4O_{12}$), or any combination thereof Illustrative phosphoric acid derivatives can include, but are not limited to, aminopolyphosphonic acids such as amino trimethylene phosphonic acid, ethylene diamine tetramethylene phosphonic acid, methylene diphosphonic acid, hydroxyethylidene diphosphonic acid, 2-phosphonobutane 1,2,4, tricarboxylic acid, or any combination thereof Other suitable phosphorous containing compounds can include, but are not limited to, phosphorous pentoxide ($P_4O_{10}$).

The acid in line 103 can be introduced to the mixer 105, in an amount sufficient to produce a mixture therein having a pH of less than about 5.5, less than about 5, less than about 4.5, less than about 4, less than about 3.5, or less than about 3. For example, the pH of the mixture can range from a low of about 2, about 2.5, or about 3 to a high of about 4, about 4.5, or about 5. The particular amount of acid and/or the particular acid(s) introduced via line 103 to the mixer 105 can be depend, at least in part, on the amount of the glycerol and/or fatty acids in the glycerol-containing feed introduced via line 101 to the mixer 105. The mole ratio of glycerol to acid can range from about 1:2 to about 50:1, from about 10:1 to about 30:1, from about 5:1 to about 20:1, or from about 10:1 to about 14:1. For example, the mole ratio of glycerol to acid can be about 20:1, about 15:1, about 10:1, about 5:1, or about 1:1.

In one or more embodiments, the acid in line 103 can be diluted with water. For example, the ratio of water to acid can range from about 0.1:1 to about 50:1, about 1:1 to about 30:1, about 2:1 to about 20:1, about 3:1 to about 10:1, or about 1:1 to about 5:1. In another example, the ratio of water to acid can be about 1:1, about 2:1, about 3:1, about 4:1, about 5:1, about 6:1, about 7:1, about 8:1, about 9:1, or about 10:1. The additional water can help reduce and/or prevent the formation of methylphosphoric acid if the glycerol-containing feed in line 101 includes any methanol.

Decreasing the pH of the glycerol-containing feed in line 101 by mixing, blending, contacting, or otherwise combining the one or more acids of line 103 therewith facilitates the separation of the glycerol from the glycerol-containing feed. The lower pH forms an emulsion of a first layer or "glycerol-lean portion" and a second layer or "glycerol-rich portion." The first layer can also be referred to as a "fatty acids-rich portion," and can include the fatty acids, soaps of fatty acids, and/or biodiesel from the glycerol-containing feed. The glycerol-rich portion can include the glycerol, monoglycerides, diglycerides, methanol, organic salts, inorganic salts, and/or water from the glycerol-containing feed.

The first portion or glycerol-lean portion via line 107 and the second portion or glycerol-rich portion via line 109 can be recovered from the mixer 105. The glycerol-rich portion in line 109 can have a glycerol concentration ranging from a low of about 30 wt %, about 40 wt %, or about 45 wt % to a high of about 55 wt %, about 60 wt %, about 65 wt %, about 75 wt %, about 85 wt %, about 95 wt %, or about 99 wt %. The glycerol-rich portion in line 109 can have a methanol concentration ranging from a low of about 1 wt %, about 5 wt %, or about 10 wt % to a high of about 25 wt %, about 35 wt %, or about 45 wt %. The glycerol-rich portion in line 109 can have a water concentration ranging from a low of about 5 wt %, about 10 wt %, or about 15 wt % to a high of about 20 wt %, about 35 wt %, or about 40 wt %. The glycerol-rich portion in line 109 can have a salt concentration ranging from a low of about 0.5 wt %, about 1 wt %, or about 2 wt % to a high of about 5 wt %, about 10 wt %, or about 15 wt %. The glycerol-rich portion in line 109 can also include residual or trace amounts of monoglycerides, proteins, amino acids, and/or gums, for example. The glycerol-rich portion in line 109 can have a fatty acids concentration of less than about 15 wt %, less than about 10 wt %, less than about 5 wt %, less than about 3 wt %, less than about 1 wt %, or less than about 0.5 wt %.

The glycerol-rich portion via line 109 can be introduced to a reactor 115. Should the glycerol-containing feed in line 101 be free of fatty acids and soaps of fatty acids, the glycerol-containing feed can bypass the mixer 105 and can be introduced directly to the separator/reactor 115. If methanol is present and it is desirable to remove methanol or at least a portion thereof from the glycerol-rich portion in line 109, the glycerol-rich portion can be heated within the reactor 115 to a temperature ranging from about 65° C. to about 95° C. Heating the glycerol-rich portion to a temperature greater than about 65° C. or more can vaporize the methanol, which can be recovered via line 117. Recovering at least a portion of the methanol, if present, from the glycerol-rich portion in line 109 can produce a methanol-lean glycerol-rich portion within the reactor 115. If methanol is present in the glycerol-rich portion of line 109, the amount of methanol removed can produce a methanol-lean glycerol-rich portion within the reactor 115 that contains less than about 5 wt %, less than about 3 wt %, less than about 2 wt %, about less than 1 wt % methanol, less than about 0.5 wt %, or less than about 0.1 wt %. In at least one specific embodiment, all methanol, if present, can be removed from the glycerol-rich portion.

After removing at least a portion of the methanol, if present, from the glycerol-rich portion within the reactor 115 one or more acids via line 111 can be introduced to the reactor 115. The acid in line 111 can be or include one or more phosphoric acids, derivatives thereof, or any combination thereof, which can be similar to the acids discussed and described above with reference to the acid in line 103. The acid of line 111 can react with at least a portion of the glycerol in the glycerol-rich portion of line 109 to produce a reacted product. The reacted product can be recovered via line 119. All or a portion of the glycerol in the glycerol-rich portion can react with the acid to produce glycerophosphoric acid products. In at least one specific embodiment, the reaction between the glycerol-rich portion and the acid can be carried out to only partial completion. In other words, the reacted product in line 119 can include glycerophosphoric acid, glycerol, free phosphoric acid(s), salt(s) of the phosphoric acid(s), water, organic salts, inorganic salts, or any combination thereof.

The amount of acid introduced via line 111 to the reactor 115 can depend, at least in part, on the amount of glycerol in the glycerol-rich portion introduced via line 109. For example, the mole ratio of glycerol to acid can range from about 5:1 to about 1:5, from about 2:1 to about 1:2, from about 5:1 to about 1:1, or from about 4:1 to about 1:2. In at least one specific embodiment, total amount of acid introduced via both lines 103 and 111 can provide a glycerol to acid ratio of from about 8:1 to about 1:4, about 6:1 to about 1:3, about 4:1 to about 1:2, about 4:2 to about 1:1.5, or about 4:3 to about 1:1.

Before, during, and/or after the addition of the acid via line 111 to the reactor 115 the contents of the reactor can be heated to reduce the amount of water contained therein. The water can also be recovered via line 117. Removing at least a portion of any water contained in the glycerol-rich portion and/or the reacted product within the reactor 115 can include heating the contents of the reactor 115 to a temperature ranging from a low of about 90° C., about 93° C., or about 95° C. to a high of about 100° C., about 105° C., or about 110° C. For example, prior to introducing the acid via line 111 the glycerol-rich portion within the reactor 115 can be heated to reduce the concentration of water therein. As such, both methanol and water can be recovered from the reactor via line 117. In another example, prior to introducing the acid via line 117, but after removing at least a portion of any methanol via line 117 from the glycerol-rich portion, the glycerol-rich portion within the reactor 115 can be heated to a temperature of about 90° C. to about 110° C. to remove at least a portion of any water therein via line 117. In yet another example, at least a portion of the methanol can be removed via line 117, acid via line 111 can be introduced to the reactor 115, and the reactor 115 can then be heated to a temperature of about 90° C. to about 110° C. to remove at least a portion of any water therein via line 117. The amount of water that can be removed from the glycerol-rich portion, the methanol-lean glycerol-rich portion, or the reacted product can produce a mixture having less than about 15 wt %, less than about 12 wt %, less than about 10 wt %, less than about 8 wt %, or less than about 5 wt % water. For example, the water concentration of the reacted product produced by removing at least a portion of any methanol via line 117 and then introducing the acid via line 111 can range from about 4 wt % to about 13 wt %.

The concentration of glycerophosphoric acid in the reacted product in line 119 can range from a low of about 1 wt % to a high of about 100 wt %. The concentration glycerol in the reacted product can range from a low of about 0 wt % to a high of about 50 wt %. The concentration of free phosphoric acid(s) can range from a low of about 0 wt % to a high of about 50 wt %. The concentration of salt(s) of the phosphoric acid(s) can range from a low of about 0 wt % to a high of about 50 wt %. The concentration of water in the reacted product can range from a low of about 0 wt % to a high of about 14 wt %. The concentration of organic and/or inorganic salt(s) can range from a low of about 0 wt % to a high of about 10 wt %. In at least one embodiment, the reacted product in line 119 can include minor or residual amounts of methylphosphoric acid. For example, the reacted product in line 119 can include about 3 wt % or less, about 2 wt % or less, about 1 wt % or less, about 0.5 wt % or less, or about 0.1 wt % or less methylphosphoric acid. In at least one specific embodiment, the reacted product in line 119 can be free or substantially free, i.e., less than 1 wt %, of any one or more of glycerol, free phosphoric acid, salt(s) of the phosphoric acid(s), water, organic and/or inorganic salt(s), and methylphosphoric acid.

The reacted product in line 119 can also have a pH of less than about 4, less than about 3.5, less than about 3, less than about 2.5, less than about 2, or less than about 1. The pH of the reacted product can also range from a low of about 0, about 1.5, or about 2 to a high of about 2.5, about 3, about 3.5, or about 4.

The reacted product in line 119, can also have a flash point greater than about 30° C., greater than about 38° C., greater than about 50° C., greater than about 66° C., or greater than about 93° C. and less than about 300° C., less than about 250° C., or less than about 200° C. For example, the reacted product in line 119 can have a flash point of about 32° C., about 54° C., about 60° C., about 68° C., about 75° C., or about 95° C. The reacted product in line 119 can also have a freezing point of less than about −25° C., less than about −50° C., less than about −60° C., or less than about −65° C.

The reacted product via line 119 can be recovered as a final product via line 121. The reacted product via line 119 can be introduced via line 123 to one or more mixers 130. A portion of the reacted product in line 119 can be recovered as a final product via line 121 and a portion of the reacted product in line 119 can be introduced via line 123 to the one or more mixers 130.

All or a portion of the reacted product in line 119 can be introduced via line 123 and a base compound via line 125 can be introduced to the mixer 130 to produce a neutralized product therein. In other words, the pH of the reacted product introduced via line 123 to the mixer 130 can be increased to produce a neutralized product via line 133. The amount of base or base compound via line 125 introduced to the mixer 130 can be sufficient to produce a "neutralized" product having a pH ranging from a low of about 5.5, about 6, or about 6.5 to a high of about 7, about 7.5, or about 8. The neutralized product can be recovered via line 133 from the mixer 130. In another example, the pH of the reacted product introduced via line 123 to the mixer 130 can be increased to greater than about 7, greater than about 8, greater than about 9, greater than about 10, greater than about 11, or greater than about 12. For example, the pH of the reacted product can be increased to a pH ranging from about 5.5 to about 12, about 7 to about 12, about 9 to about 12, about 10 to about 12, or about 8.5 to about 11. As such, a basic product can also be recovered via line 133 from the mixer 130. The particular base compound or combination of base compounds and the amount(s) thereof that can be added to the reacted product within the mixer 130 can depend, at least in part, on the amount of the particular composition or make-up of the reacted product, i.e., the particular components and the relative amount of those components contained in the reacted product.

Figure 2:
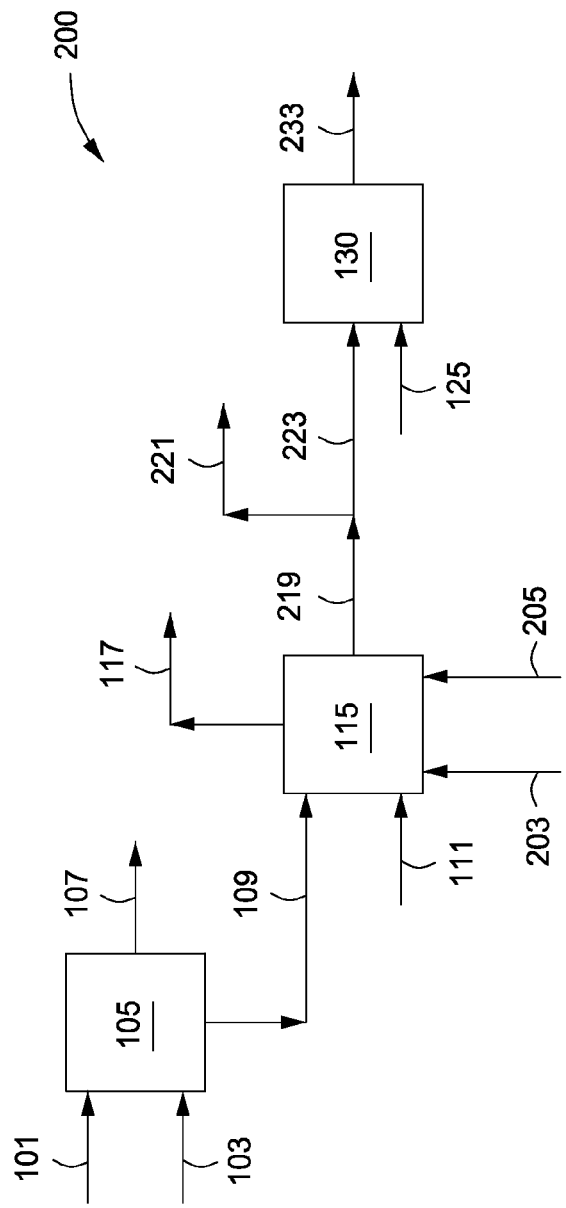
FIG. 2 depicts another illustrative system for processing glycerol, according to one or more embodiments described.

The base compound in line 125 can be or include any base or combination of two or more bases. Illustrative bases or base compounds in line 125 can include, but are not limited to, potassium hydroxide (KOH), sodium hydroxide (NaOH), lithium hydroxide (LiOH), amines, or any combination thereof. Amines can include, but are not limited to, alkanolamines, polyamines, aromatic amines, and any combination thereof. Illustrative alkanolamines can include, but are not limited to, monoethanolamine ("MEA"), diethanolamine ("DEA"), triethanolamine ("TEA"), or any combination thereof. Illustrative aromatic amines can include, but are not limited to, benzyl amine, aniline, ortho toludine, meta toludine, para toludine, n-methyl aniline, N-N'-dimethyl aniline, di- and tri-phenyl amines, 1-naphthylamine, 2-naphthylamine, 4-aminophenol, 3-aminophenol and 2-aminophenol. Illustrative polyamines can include, but are not limited to, diethylenetriamine ("DETA"), triethylenetetramine ("TETA"), tetraethylenepentamine ("TEPA") 1,3-propanediamine, 1,4-butanediamine, polyamidoamines, and polyethylenimines FIG. 2 depicts another illustrative system 200 for processing glycerol, according to one or more embodiments. The system 200 can be similar to the system 100 discussed and described above with reference to FIG. 1. As discussed above, the glycerol-containing feed via line 101 and the acid via line 103 can be introduced to the one or more mixers 105, where the two components can be mixed, blended, contacted, or otherwise combined together to produce a mixture and separated into at least two fractions or portions. From the mixer 105, the first portion or glycerol-lean portion via line 107 and the glycerol-rich portion via line 109 can be recovered from the mixer 105. The glycerol-rich portion via line 109 can be introduced to the reactor 115 and methanol and/or water via line 117 can be removed therefrom. The acid via line 111 can be introduced to the reactor 115 to produce the reacted product therein, which can be as discussed and described above with reference to FIG. 1.

The reactor 115 in the system 200 can further include one or more additional lines in fluid communication therewith (two are shown 203, 205). One or more oxidants via line 203 can be introduced to the reactor 115. One or more catalysts via line 205 can be introduced to the reactor 115. In still another example, both one or more oxidants via line 203 and one or more catalysts via line 205 can be introduced to the reactor 115. The oxidant and/or the catalyst can react with the reacted product at conditions sufficient to produce an oxidized product via line 219.

The one or more oxidants in line 203 can include, but are not limited to, hydrogen peroxide ($H_2O_2$), oxygen ($O_2$), ozone ($O_3$), oxygen-containing gases, e.g., air, sodium permanganate, potassium permanganate, sodium persulfate, potassium persulfate, magnesium peroxide, calcium peroxide, sodium percarbonate, or any combination thereof. The amount of oxidant introduced via line 203 to the reactor 115 can vary. The amount of oxidant introduced via line 203 to the reactor 115 can be sufficient to at least partially oxidize the glycerophosphoric acid to produce phosphoglyceric acid. In at least one specific embodiment, the amount of oxidant introduced via line 203 to the reactor 115 can be less than the amount required for complete oxidation of the reacted product therein. In other words, the oxidized product in line 219 can be a partially oxidized product. The amount of oxidant introduced via line 203 can depend, at least in part, on the amount of the glycerol-rich portion introduced via line 109 to the reactor 115 and/or the particular composition or make-up of the reacted product produced by reacting the glycerol-rich portion with the one or more acids introduced via line 111. The particular composition or make-up of the glycerol-rich portion and/or the reacted product can include the particular components and the relative amount of those components contained therein. The amount of oxidant introduced via line 203, based on the number of moles oxidant per mole of glycerophosphoric acid, can range from a low of about 0.1, about 0.5, or about 1 to a high of about 1.5, about 2, about 2.5, or about 3.

In at least one specific embodiment, the one or more catalysts via line 205 can be introduced to the reactor 115, in addition to or in lieu of the oxidant via line 203, to produce the oxidized or partially oxidized product via line 219. For example, hydrogen peroxide via line 203 and a catalyst, e.g., ferrous sulfate, via line 205 can be introduced to the reactor 115. Other catalysts via line 205 that can be used in lieu of or in addition to the oxidant in line 203 can include, but are not limited to, carbon supported platinum, carbon supported palladium, silicates, aluminophosphates, or any combination thereof.

The glycerol-rich portion via line 109, acid via line 111, oxidant via line 203, and/or the catalyst via line 205 can be introduced to the reactor 115 in any order or sequence. For example, the glycerol-rich portion via line 109 and the acid via line 111 can be mixed and reacted within the reactor 115 to produce the reacted product therein. After producing the reacted product the oxidant via line 203 and/or the catalyst via line 205 can be introduced to the reactor 115 to produce the oxidized product therein. In another example, the glycerol-rich portion via line 109, the acid via line 111, and the oxidant via line 203 can be introduced to the reactor 115 at the same or substantially the same time and mixed and reacted together with in the reactor 115 to produce the oxidized product therein. In another example, the oxidant via line 203 and/or the catalyst via line 205 can be introduced to the reactor 115 and mixed with the glycerol-rich portion prior to removal of any methanol that can be contained in the glycerol-rich portion and the addition of the acid via line 111.

In at least one specific embodiment, at least a portion of the glycerol-rich portion and acid and/or the reacted product can react with the oxidant, the catalysts, or both, at conditions sufficient to produce the oxidized product via line 219 that can include, but is not limited to, carboxylic acids, hydroxyl carboxylic acids, dicarboxylic acids, phosphoglyceric acid, glycerophosphoric acid, free glycerol, free phosphoric acid, water, glyceric acid, oxalic acid, glycolic acid, formic acid, glyceraldehydes, hydroxypyruvic acid, tartronic acid, derivatives thereof, or any combination thereof. In one or more embodiments, at least a portion of the methanol, if present, can react with the oxidant at conditions sufficient to produce formic acid. Suitable conditions include a temperature of about 70° C. or less, about 65° C. or less, about 60° C. or less, or about 55° C. or less. For example, the reaction temperatures can range from a low of about 0° C., 15° C., or 20° C. to a high of about 50° C., 65° C., or 75° C., although higher temperatures are envisaged.

The particular makeup or composition of the oxidized product in line 219 can widely vary. The oxidized product in line 219 can have a concentration of phosphoglyceric acid ranging from a low of about 1 wt % to a high of about 100 wt %. The oxidized product in line 219 can have a concentration of glycerophosphoric acid ranging from a low of about 1 wt % to a high of about 50 wt %. The oxidized product in line 219 can have a concentration of free glycerol ranging from a low of about 1 wt % to a high of about 50 wt %. The oxidized product in line 219 can have a concentration of carboxylic acids ranging from a low of about 1 wt % to a high of about 50 wt %. The oxidized product in line 219 can have a concentration of hydroxyl carboxylic acids ranging from a low of about 1 wt % to a high of about 30 wt %. The oxidized product in line 219 can have a concentration of dicarboxylic acids ranging from a low of about 1 wt % to a high of about 40 wt %. The oxidized product in line 219 can have a concentration of free phosphoric acid ranging from a low of about 1 wt % to a high of about 40 wt %. The oxidized product in line 219 can have a concentration of water ranging from a low of about 1 wt % to a high of about 14 wt %. The oxidized product in line 219 can have a concentration of glyceric acid ranging from a low of about 1 wt % to a high of about 50 wt %. The oxidized product in line 219 can have a concentration of oxalic acid ranging from a low of about 1 wt % to a high of about 5 wt %. The oxidized product in line 219 can have a concentration of glycolic acid ranging from a low of about 1 wt % to a high of about 10 wt %. The oxidized product in line 219 can have a concentration of formic acid ranging from a low of about 1 wt % to a high of about 40 wt %. The oxidized product in line 219 can have a concentration of glyceraldehydes acid ranging from a low of about 1 wt % to a high of about 1 wt %. The oxidized product in line 219 can have a concentration of hydroxypyruvic acid ranging from a low of about 1 wt % to a high of about 20 wt %. The oxidized product in line 219 can have a concentration of tartronic acid ranging from a low of about 1 wt % to a high of about 30 wt %. In one or more embodiments, the oxidized product can be free or substantially free, i.e., less than 1 wt %, of any one or more of glycerophosphoric acid, free glycerol, carboxylic acids, hydroxyl carboxylic acids, dicarboxylic acids, free phosphoric acid, water, oxalic acid, glycolic acid, formic acid, glyceraldehydes acid, hydroxypyruvic acid, and tartronic acid.

The oxidized product via line 219 can be recovered as a final product via line 221. The oxidized product via line 219 can be introduced via line 223 to one or more mixers 130, which can be similar to the mixer 130 discussed and described above with reference to FIG. 1. A portion of the oxidized product in line 219 can be recovered as a final product via line 221 and a portion of the oxidized product in line 219 can be introduced via line 223 to the one or more mixers 130.

All or a portion of the oxidized product in line 219 can be introduced via line 223 and a base compound via line 125 can be introduced to the mixer 130 to produce a neutralized product therein. In other words, the pH of the oxidized product introduced via line 223 to the mixer 130 can be increased to produce a neutralized oxidized product. The amount of base or base compound via line 125 introduced to the mixer 130 can be sufficient to produce a "neutralized" oxidized product having a pH ranging from a low of about 5.5, about 6, or about 6.5 to a high of about 7, about 7.5, or about 8. The neutralized oxidized product can be recovered via line 233 from the mixer 130. In another example, the pH of the oxidized product introduced via line 223 to the mixer 130 can be increased to greater than about 7, greater than about 8, greater than about 9, greater than about 10, greater than about 11, or greater than about 12. For example, the pH of the oxidized product can be increased to a pH ranging from about 5.5 to about 12, about 7 to about 12, about 9 to about 12, about 10 to about 12, or about 8.5 to about 11. As such, a basic oxidized product can also be recovered via line 133 from the mixer 130. The base compound in line 125 can be as discussed and described above with reference to FIG. 1. The particular base compound or combination of base compounds and the amount(s) thereof that can be added to the reacted product within the mixer 130 can depend, at least in part, on the amount of the particular composition or make-up of the oxidized product, i.e., the particular components and the relative amount of those components contained in the oxidized product.

The systems 100 and 200, as discussed and described above can include the mixer 105, reactor 115, and mixer 130. However, any two or more of the mixer 105, reactor 115, and mixer 130 can be combined into a single unit. In other words, the mixing, separation, e.g., the separation of the glycerol-lean portion via line 107 from the mixer 105 and the separation of the methanol and/or water via line 117 from the reactor 115, and/or the mixing of the base via line 125 and the reacted product via line 123 or the reacted product via line 223 can take place in a single vessel, two vessels, or as shown in FIGS. 1 and 2, a plurality of vessels. The depiction of multiple vessels, i.e., the mixer 105, reactor 115, and mixer 130, while suitable for the processing of glycerol, is also preferable for clarity and ease of description. Accordingly any two or more of the steps discussed and described above can be carried out in a single vessel or any number of vessels.

The mixers 105, 130 can be any device or system suitable for batch, intermittent, and/or continuous mixing of two or more components. For example, the mixer 105 can be any device or system suitable for mixing the glycerol-containing fee in line 101 and the acid in line 104. The mixers 105, 130 can be capable of producing a homogenized mixture. Illustrative mixers can include, but are not limited to, mechanical mixer agitation, ejectors, static mixers, mechanical/power mixers, shear mixers, sonic mixers, or combinations thereof. The mixers 105, 130 can operate at temperatures of about 25° C. to about 150° C. The mixers 105, 130 can include one or more heating jackets, heating coils, internal heating elements, cooling jacks, cooling coils, internal cooling elements, or the like, which can heat the mixture to a temperature of from about 25° C. to about 150° C., for example. Should methanol be contained in the glycerol-containing feed in line 101 and the mixer 105 heats the mixture to a temperature greater than the boiling point of methanol, a methanol recovery line can be in fluid communication with the mixer 130 to recover the vaporized methanol as a product. Similarly, water can be recovered from the mixer 130.

The reactor 115 can be any container or environment suitable for batch, intermittent, and/or continuous contacting of the glycerol-rich portion in line 108 with the oxidant in line 110 and/or the catalyst in line 112. The reactor 110 can be an open vessel or a closed vessel. The reactor 110 can include one or more mixing devices such as one or more mechanical/power mixers and/or acoustic mixers such as sonic mixers. The reactor 110 can include a cooling jacket and/or coil for maintaining a temperature of the reaction mixture below a predetermined temperature. The reactor 110 can include one or more nozzles, fluid distribution grids, or other device(s) for introducing the oxidant to the reactor 110.

The products, i.e., the reacted product in line 121, the neutralized reacted product in line 133, the oxidized product in line 221 and/or the neutralized oxidized product in line 233, can be used in a number of applications as produced, diluted, and/or mixed with other compounds, fluids, or components. The products in lines 121, 133, 221, and/or 233 can be diluted with water, for example. In another example, the products in lines 121, 133, 221, and/or 233 can be mixed or blended with corrosion inhibitors, polymers, salts, scale removers, surfactants, inhibitors, or any combination thereof. In another example, the products in lines 121, 133, 221, and/or 233 can be mixed or blended with water, corrosion inhibitors, polymers, slats, scale removers, surfactants, inhibitors, or any combination thereof. The amount of the products in lines 1121, 133, 221, and/or 233 that can be admixed with a particular component can depend, at least in part, on the particular composition of that fluid and the conditions of temperature and pressure to which the fluid mixture can be subjected. As such, once the particular system and the conditions of the system have been determined, the particular amount of product via lines 121, 133, 221, and/or 233 that can be introduced to that system and the desired amount of any other component that can be mixed therewith can be determined.

One particular use or application of the products in lines 121, 133, 221, and/or 233 can be to remove, inhibit, and/or reduce inorganic mineral scale deposits ("scale"). The formation of scales can be caused by a number of factors, which can include, but are not limited to, pressure drops, temperature fluctuations, changes in pH or ionic strength, and any combinations thereof. The products in line 121, 133, 221, and/or 233 can act or work as an acid, a sequestrant, a chelant, a dispersing agent, a solvent, or any combination thereof for removing scale(s). The products in line 121, 133, 221, and/or 233 can be prevent or inhibit the formation of scales.

In the context of oilfield operations, commonly encountered scales include, but are not limited to, calcium carbonate ($CaCO_3$), calcium sulfate ($CaSO_4$), barium sulfate ($BaSO_4$); and sodium chloride (NaCl). Other inorganic mineral deposits can include, strontium sulfate ($SrSO_4$), strontium carbonate ($SrCO_3$), iron oxide ($Fe_2O_3$), iron carbonate ($FeCO_3$), iron sulfide (FeS), barium-strontium sulfate ($BaSr(SO_4)_2$), magnesium carbonate ($MgCO_3$), magnesium sulfate ($MgSO_4$), or any combination thereof. For example, the reacted product in line 116 can remove barium sulfate deposits in an amount of about 1,000 ppm, about 2,500 ppm, about 4,000 ppm, about 5,000 ppm, about 6,000 ppm, about 7,000 ppm, or about 8,000 ppm barium sulfate.

The formation or precipitation of scale deposits can occur in, for example, oil production and/or processing equipment, which can be located above and/or below the surface. The formation or precipitation of scale deposits can also occur in subterranean formations, such as an oil and/or gas producing formations. Oil production and processing equipment can include, flow lines, heaters, pumps, valves, pipes, pipelines, risers, drill strings, wellbores, downhole pumps, perforations, fractures, fissures, and the like. Other areas in which scale deposits can be problematic include, but are not limited to, the chemical processing industries, public utilities, and other processes in which mineral-laden water is processed or used, as in heat exchangers, storage vessels, piping, reactors, evaporators, and the like.

Introducing the products in lines 121, 133, 221, and/or 233 to equipment, formations, and/or other locations where scale deposits form or can potentially form can reduce scale and/or inhibit or prevent the formation of scale. The products, at any desired concentration, can be used to remove scale and/or prevent or reduce the formation of scale. The products in lines 121, 133, 221, and/or 233 can be diluted with water to have a water concentration of from about 1 wt % to about 99 wt %, for example. The products in lines 121, 133, 221, and/or 233 can be diluted with water, as needed, to produce a reacted product having a desired concentration.

In one or more embodiments, the products in lines 121, 133, 221, and/or 233 can be used to demulsify an emulsion. The products 133 and/or 233, for example, can demulsify an emulsion by lowering the pH of the emulsion and/or by increasing the specific gravity of the produced water. The products can be used as produced, diluted, and/or mixed with other ingredients that can improve the demulsification. Illustrative additional ingredients or additives that can be added to the products to improve or facilitate demulsification of an emulsion can include, but are not limited to, silicon compounds, glycols, salts, any other water soluble demulsifiers, or any combination thereof.

In one or more embodiments, the products in lines 121, 133, 221, and/or 233 can be used as a frac fluid, drilling fluid, or component thereof for oil and gas production. The products in lines 121, 133, 221, and/or 233 can be used neat or mixed or blended with one or more other fluids. An illustrative frac fluid, for example, can include about 5-25 wt % of one or more of the products in lines 121, 133, 221, and/or 233, about 5-25 wt % formic acid, about 5-25 wt % reacted product, and about 45-65 wt % water. Illustrative blending agents and/or additives can include, but are not limited to, drilling fluids, steam, corrosion inhibitors, water, acids such as hydrochloric acid, surfactants, polymers such as polyols, polyamides, poly celluloses, poly(acrylic acids), or any combination thereof. For drilling, the products can be particularly useful in water-based drilling fluids.

In one or more embodiments, the products in lines 121, 133, 221, and/or 233 can be used as an anti-icing compound. The products can be used neat, diluted with water, or blended with one or more additives. In at least one specific embodiment, the anti-icing compound can be sprayed, injected, or otherwise introduced on or to pipelines, processing equipment, diluents for chemicals, storage tanks, ships, oil rigs, trucks, and storage equipment, for example.

In one or more embodiments, the products in lines 121, 133, 221, and/or 233 can be used as a general purpose cleaner. As a general purpose cleaner, the products can be used neat, diluted with water, or blended with one or more additives. Suitable additives can include, but are not limited to, polymers, salts, and/or other treatment chemicals that can expand or enhance one or more functional properties of the reacted products. In at least one specific embodiment, the products can be diluted with water to produce a cleaning solution having a concentration of the reacted product ranging from about 100 ppmw to about 40 wt %.

In one or more embodiments, the products in lines 121, 133, 221, and/or 233 can be used to prevent or reduce the formation of hydrates in a fluid containing one or more hydrate-forming constituents by contacting the fluid with the reacted product(s). For example, the neutralized reacted via line 133 and/or the neutralized oxidized products via line 233 can be introduced to a fluid or system that contains hydrates or in which hydrates can potentially form, e.g., a hydrocarbon gas stream containing methane and/or natural gas. Illustrative systems can include, but are not limited to, hydrocarbon production/processing equipment, pipelines, storage tanks, and the like. In at least one specific embodiment, the reacted products can be introduced into a downhole location such as a hydrocarbon production well to control hydrate formation in fluids produced therefrom. In another example, the products can be introduced to a produced hydrocarbon at a wellhead location or into a riser through which produced hydrocarbons are transported in offshore operations from the ocean floor to an offshore production facility. In still another example, the products can be introduced to a hydrocarbon prior to transporting the hydrocarbon, for example, via a subsea pipeline from an offshore production facility to an onshore gathering and/or processing facility. In one or more embodiments, the products can be introduced to a downhole location as a drilling fluid or as a component of a drilling fluid.

In one or more embodiments, the products in lines 121, 133, 221, and/or 233 can be used to recover a gas that is bound or entrained in a formed hydrate. In at least one specific embodiment, the neutralized reacted product via line 121 and/or the neutralized oxidized product via line 233 can be introduced into a downhole location or any other location that contains or may contain hydrates where the second reacted product can release at least a portion of any gases bound or contained in the hydrate(s) present therein. The released gases bound in the hydrate(s) can be recovered as a product.

A mixture that can potentially form or contain hydrates can include, for example a water and gas mixture. The gas can be a hydrocarbon normally gaseous at 25° C. and 100 kPa, such as an alkane of 1-4 carbon atoms, e.g., methane, ethane, propane, n-butane, isobutane, or an alkene of 2-4 carbon atoms e.g., ethylene, propylene, n-butene, isobutene, or any combination thereof. The gas can include about 80 wt %, about 90 wt %, or more methane. The gas can also include about 0.1 wt % to about 10 wt % $C_2$ hydrocarbons and about 0.01 wt % to about 10 wt % $C_3$ hydrocarbons.

In one or more embodiments, the products via line 121, 133, 221, and/or 233 can be used to remove existing corrosion within a system. In one or more embodiments, the products via line 121, 133, 221, and/or 233 can be used to reduce or prevent corrosion within a system. For example the products via line 121, 133, 221, and/or 233 can be used to reduce or prevent corrosion within a pipeline or riser. The products in lines 121, 133, 221, and/or 233 can deposit or otherwise form a protective layer on a metal surface that can reduce or prevent corrosion of the metal surface.

In one or more embodiments, the reacted product via line 121 and/or the oxidized product via line 221 can be used to unswell or otherwise reduce the size of clay and/or polymer particles that have been introduced to a formation. Illustrative clays that can be unswelled with the reacted product in line 121 and/or the oxidized product in line 221 can include, but are not limited to, chlorite clays, illite clays, kaolinite clays, smectite clays such as montomorillonite, bentonite clays such as sodium bentonite, calcium bentonite, and potassium bentonite, or any combination thereof. Illustrative polymers that can be unswelled with the reacted product in line 121 and/or the oxidized product in line 221 can include, but are not limited to, polyacrylic acid (PAA), polymethacrylic acid (PMA), poly maleic anhydride, polyvinyl alcohol (PVOH), polyamides, low-viscosity latex, or any combination thereof. Other polymers that can be unswelled with the reacted product in line 121 and/or the oxidized product in line 221 can include polyethylene oxide, polypropylene oxide, polyoxymethylene, polyvinyl methyl ether, polyethylene imide, polyvinyl alcohol, polyvinyl pyrrolidone, polyethyleneimine, polyethylene sulfonic acid, polysilicic acid, polyphosphoric acid, polystyrene sulfonic acid, polyvinylamine, natural water soluble polymers, guar derivatives, cellulose derivatives, xanthan, chitosan, diutan, any suitable copolymers, or mixtures thereof. The reacted product in line 121 and/or the oxidized product in line 221 can reduce the volume or size of a swelled clay and/or polymer particle by about 2%, about 4%, about 6%, about 8%, about 10%, about 12%, about 14%, about 16%, about 18%, or about 20%.

EXAMPLES

To provide a better understanding of the foregoing discussion, the following non-limiting examples are provided. Although the examples are directed to specific embodiments, they are not to be viewed as limiting the invention in any specific respect. All parts, proportions and percentages are by weight unless otherwise indicated.

Example I

A reacted product was prepared from a glycerol-containing feed that had a composition of 1.17 wt % potassium sulfate, 14 wt % methanol, 25 wt % fatty acids, 10 wt % water, and 49.83% glycerol. The moles of glycerol in the glycerol-containing feed were calculated and an equal number of moles of phosphoric acid were measured out to produce a glycerol-containing feed to phosphoric acid molar ratio of 1:1. About 10% of the phosphoric acid was mixed with four parts water to produce a diluted phosphoric acid solution. The diluted phosphoric acid solution was added to and mixed with the glycerol-containing feed. The pH of the glycerol-containing feed was lowered from 11 to less than 3. The mixture was then heated to a temperature of about 100° F. and the fatty acids separated to the top of the mixture and were removed. The components remaining in the mixture were the glycerol, water, salts, phosphoric acid, and methanol. The mixture was then heated to a temperature of about 150° F. to remove the methanol therefrom. The additional water added to the phosphoric acid prevented the formation of methylphosphoric acid during the heating used to remove the methanol. Methylphosphoric acid exhibits beneficial properties, but since methylphosphoric acid is not soluble in water it can be desirable to remove the methanol from the mixture. After the methanol was removed the remaining phosphoric acid, i.e., the remaining 90%, was added to the mixture. The mixture was then heated to a temperature of about 200° F. to about 220° F. during which water was driven off. The mixture was heated until the water content of the solution was about 8.7 wt %. The resulting reacted product was a viscous, amber colored mixture that had a gravity of 1.58 g/L at 60° F. and a refractive index (RI) of 1.4598 at 60° F.

The reacted product was mixed with an equal amount of water to produce diluted reacted product. The freezing point of the diluted reacted product was less than −30° F. The diluted reacted product was then tested on three different types of scales and two corroded metals.

The removal of calcium carbonate scale (Ex. 1), calcium sulfate scale (Ex. 2a and 2b), and barium sulfate scale (Ex. 3) were evaluated. In each example, reacted product was contacted with the scale and the results were evaluated. In Example 1 about 2.7 g of a calcium carbonate scale recovered from an east Texas oil well was placed in a beaker with 50 mL of the diluted reacted product at a temperature of 140° F. The calcium carbonate scale was dissolved in 3 hours. In Example 2a about 1.9 grams of a calcium sulfate scale recovered from a west Texas oil well was placed in a beaker with 50 mL of the diluted reacted product at a temperature of 140° F. The calcium sulfate scale dissolved in 5 hours. In Example 2b, which was carried out under similar conditions as in Ex. 2a, the calcium sulfate scale dissolved in 2.5 hours. In Ex. 3 about 1.92 grams of a barium sulfate scale recovered from a west Texas oil well was placed into a beaker with 50 mL of the diluted reacted product at a temperature of 140° F. After 5 hours 0.41 grams of the barium sulfate scale had dissolved.

In another example (Ex. 4), the removal of metal corrosion, i.e., rust, from iron and steel was evaluated. A rusty iron nail was placed in 100 mL of the diluted reacted product at a temperature of 72° F. After 12 hours the rust had been removed and a gray-black film of phosphate had been deposited onto the surface of the nail. In another test (Ex. 5), a piece of steel having iron sulfide scale was placed in 50 mL of the diluted reacted product at 72° F. After 12 hours the iron sulfide scale had been removed and a gray-black film of phosphate had been deposited on the surface of the steel.

Example II

A neutralized reacted product was also prepared. A portion of the reacted product prepared above in Example I was neutralized with NaOH to have a pH of 6.8. The neutralized reacted product was then mixed with an equal amount of water to produce a diluted neutralized reacted product. The freezing point of the diluted neutralized reacted product was less than −30° F.

The reduction or prevention of calcium sulfate scale (Ex. 6) and barium scale (Ex. 7) with the neutralized reacted were evaluated. In Ex. 6, about 1,000 ppm of the diluted neutralized reacted product in synthetic brine was 100% effective in preventing the formation of calcium sulfate scale. In Ex. 7, about 1,000 ppm of the diluted neutralized reacted product was found to be about 90% effective in preventing the formation of barium scale. The tests were carried out according to the standard test procedures discussed and described in U.S. Pat. No. 5,167,828.

The removal of metal corrosion, i.e., rust, (Ex. 8) from iron was also evaluated. In Ex. 8 a rusty nail was placed in 100 mL of the diluted neutralized reacted product and left at room temperature. After four days the rust was completely removed from the nail and a protective gray-black phosphate layer had been deposited on the surface of the nail.

Example III

An exemplary oxidized product was also prepared from the glycerol-containing feed used in Example I that had a composition of 1.17 wt % potassium sulfate, 14 wt % methanol, 25 wt % fatty acids, 10 wt % water, and 49.83 wt % glycerol. The moles of glycerol in the glycerol-containing feed were calculated and an equal number of moles of phosphoric acid were measured out to produce a glycerol-containing feed to phosphoric acid molar ratio of 1:1. About 10% of the phosphoric acid was mixed with four parts water to produce a dilute phosphoric acid solution. The dilute phosphoric acid solution was added to and mixed with the glycerol-containing feed. The pH of the glycerol-containing feed was lowered from 11 to less than 3. The mixture was then heated to a temperature of about 100° F. and the fatty acids separated to the top of the mixture and were removed. The components remaining in the mixture were the glycerol, water, salts, phosphoric acid, and methanol A 50% solution of hydrogen peroxide ($H_2O_2$) was added to the mixture in an amount of about 12 wt %, based on the total weight of the mixture, and mixed for 6 hours. After mixing for 6 hours the mixture was heated to a temperature of about 150° F. to remove the methanol therefrom. After the methanol was removed the remaining phosphoric acid, i.e., the remaining 90%, was added to the mixture. The mixture was then heated to a temperature of about 220° F. during which water driven off. The mixture was heated until the water content of the solution was about 14 wt %. The resulting oxidized product was a clear, light yellow colored solution with a gravity of 1.46 g/L at 60° F. and a refractive index (RI) of 1.4405 at 60° F. The oxidized product was mixed with distilled water to produce a 40% solution of the oxidized product in water. The freezing point of the 40% solution of oxidized product was less than −30° F.

The removal of calcium sulfate (Ex. 9) was evaluated. In Ex. 9, about 2.81 g of a calcium sulfate scale recovered from an east Texas oil well was placed in a beaker with 50 mL of the 40% solution of the oxidized product at 52° F. After less than 3 hours the scale was dissolved.

The effect of the oxidized product on deswelling polymers (Ex. 10a and 10b) and clay (Ex. 11) were also conducted. In Ex. 10a, the 40% solution of the oxidized product was found to dehydrate and unswell a polyamide water soluble polymer. In Ex. 10b, the 40% solution of the oxidized product was found to dehydrate and unswell a polyacrylate water soluble polymer. In Ex. 11, the 40% solution of the oxidized product was also found to unswell bentonite clay.

Certain embodiments and features have been described using a set of numerical upper limits and a set of numerical lower limits It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for processing a glycerol-containing feed, comprising:
   separating a mixture comprising glycerol and fatty acids into a glycerol-rich portion and a fatty acids-rich portion, wherein the glycerol-rich portion comprises glycerol, methanol, and water; and
   reacting the glycerol-rich portion comprising the glycerol, methanol, and water with an acid comprising phosphorus to produce a reacted product comprising glycerophosphoric acid, any unreacted glycerol, and any unreacted acid.

2. The method of claim 1, wherein the mixture has a pH from about 6 to about 13, and wherein separating the mixture comprises decreasing the pH of the mixture to about 2 to about 5.

3. The method of claim 2, wherein the pH of the mixture is greater than about 9, and wherein the pH of the reacted product is from about 2 to about 3.5.

4. The method of claim 2, wherein water and one or more second acids is added to the mixture having a pH from about 6 to about 13 to decrease the pH of the mixture to about 2 to about 5, wherein a mole ratio of the glycerol in the mixture to the one or more second acids is about 5:1 to about 20:1, and wherein a ratio of water to the one or more second acids is from about 1:1 to about 10:1.

5. The method of claim 1, wherein a molar ratio of the glycerol in the glycerol-rich portion to the acid comprising phosphorous is from about 5:1 to about 1:5.

6. The method of claim 1, further comprising heating the glycerol-rich portion to a temperature of about 65° C. to about 90° C. before reacting the glycerol-rich portion with the acid to remove a portion of the methanol therefrom.

7. The method of claim 1, further comprising mixing the reacted product with one or more base compounds to produce a neutralized product having a pH of about 6 to about 8.

8. The method of claim 1, wherein the glycerol-rich portion comprises about 30 wt % to about 85 wt % glycerol, about 5 wt % to about 35 wt % methanol, and about 5 wt % to about 40 wt % water.

9. The method of claim 1, wherein the reacted product has a flash point of about 66° C. to about 200° C. and a freeze point of about −25° C. to about −65° C.

10. The method of claim 1, further comprising removing one or more inorganic mineral scales by contacting the one or more inorganic mineral scales with the reacted product.

11. The method of claim 1, further comprising lowering a freeze point of water by adding the reacted product to the water.

12. The method of claim 1, further comprising deswelling clay particles, polymer particles, or a combination thereof by contacting the clay particles, polymer particles, or the combination thereof with the reacted product.

13. The method of claim 1, further comprising introducing the reacted product to a wellbore as a drilling fluid or as a component of a drilling fluid.

14. The method of claim 1, further comprising removing corrosion from a metal by contacting the corrosion with the reacted product.

15. The method of claim 1, further comprising reducing a formation of hydrates in a fluid containing one or more hydrate-forming constituents by contacting the fluid with the reacted product.

16. The method of claim 1, further comprising demulsifying an emulsion by mixing the emulsion with the reacted product.

17. The method of claim 1, further comprising:
mixing the reacted product with one or more base compounds to produce a neutralized product having a pH of about 6 to about 8; and
removing one or more inorganic mineral scales by contacting the one or more inorganic mineral scales with the neutralized product.

18. The method of claim 1, further comprising:
mixing the reacted product with one or more base compounds to produce a neutralized product having a pH of about 6 to about 8; and
lowering a freeze point of water by adding the neutralized product to the water.

19. The method of claim 1, further comprising:
mixing the reacted product with one or more base compounds to produce a neutralized product having a pH of about 6 to about 8; and
deswelling clay particles, polymer particles, or a combination thereof by contacting the clay particles, polymer particles, or the combination thereof with the neutralized product.

20. The method of claim 1, further comprising:
mixing the reacted product with one or more base compounds to produce a neutralized product having a pH of about 6 to about 8; and
introducing the neutralized product to a wellbore as a drilling fluid or as a component of a drilling fluid.

21. The method of claim 1, further comprising:
mixing the reacted product with one or more base compounds to produce a neutralized product having a pH of about 6 to about 8; and
removing corrosion from a metal by contacting the corrosion with the neutralized product.

22. The method of claim 1, further comprising:
mixing the reacted product with one or more base compounds to produce a neutralized product having a pH of about 6 to about 8; and
reducing a formation of hydrates in a fluid containing one or more hydrate-forming constituents by contacting the fluid with the neutralized product.

23. The method of claim 1, further comprising:
mixing the reacted product with one or more base compounds to produce a neutralized product having a pH of about 6 to about 8; and
demulsifying an emulsion by mixing the emulsion with the neutralized product.

24. A method for processing a glycerol-containing feed, comprising:
decreasing a pH of a biodiesel byproduct comprising fatty acids, glycerol, water, methanol, inorganic salts, and organic salts to produce a mixture comprising a glycerol-rich portion and a fatty acids-rich portion, wherein the glycerol-rich portion comprises glycerol, methanol, water, organic salts, and inorganic salts;
removing a portion of the methanol contained in the glycerol-rich portion to produce a methanol-lean glycerol-rich portion comprising the glycerol, water, and a remaining portion of the methanol; and
reacting at least a portion of the methanol-lean glycerol-rich portion comprising the glycerol, water, and the remaining portion of the methanol with a first acid to produce a reacted product comprising glycerophosphoric acid, any unreacted glycerol, and any unreacted first acid.

25. The method of claim 24, wherein decreasing the pH of the biodiesel byproduct comprises mixing the biodiesel byproduct with a second acid.

26. The method of claim 24, wherein the glycerol-rich portion comprises about 30 wt % to about 85 wt % glycerol, about 5 wt % to about 35 wt % methanol, and about 5 wt % to about 40 wt % water.

27. The method of claim 24, further comprising:
removing one or more inorganic mineral scales by contacting the one or more inorganic mineral scales with the reacted product;
lowering a freeze point of water by adding the reacted product to the water;
deswelling clay particles, polymer particles, or a combination thereof by contacting the clay particles, polymer particles, or the combination thereof with the reacted product;
introducing the reacted product to a wellbore as a drilling fluid or as a component of a drilling fluid;
removing corrosion from a metal by contacting the corrosion with the reacted product;
reducing a formation of hydrates in a fluid containing one or more hydrate-forming constituents by contacting the fluid with the reacted product; or
demulsifying an emulsion by mixing the emulsion with the reacted product.

28. The method of claim 24, further comprising mixing the reacted product with one or more base compounds to produce a neutralized product having a pH of about 6 to about 8; and
removing one or more inorganic mineral scales by contacting the one or more inorganic mineral scales with the neutralized product;
lowering a freeze point of water by adding the neutralized product to the water;
deswelling clay particles, polymer particles, or a combination thereof by contacting the clay particles, polymer particles, or the combination thereof with the neutralized product;
introducing the neutralized product to a wellbore as a drilling fluid or as a component of a drilling fluid;
removing corrosion from a metal by contacting the corrosion with the neutralized product;
reducing a formation of hydrates in a fluid containing one or more hydrate-forming constituents by contacting the fluid with the neutralized product; or
demulsifying an emulsion by mixing the emulsion with the neutralized product.

29. A method for processing a glycerol-containing feed, comprising:
mixing a biodiesel byproduct having a pH of about 6 to about 13 with a sufficient amount of a first acid comprising phosphorus to produce a mixture having a pH of about 2 to about 5, wherein the biodiesel byproduct comprises fatty acids, glycerol, methanol, and water;
separating the mixture into a glycerol-rich portion and a fatty acids-rich portion, wherein the glycerol-rich portion comprises about 30 wt % to about 85 wt % glycerol, about 5 wt % to about 35 wt % methanol, and about 5 wt % to about 40 wt % water; and reacting at least a portion of the glycerol-rich portion comprising about 30 wt % to about 85 wt % glycerol, about 5 wt % to about 35 wt % methanol, and about 5 wt % to about 40 wt % water with a second acid comprising phosphorus at conditions sufficient to produce a reacted product comprising glycerophosphoric acid, water, any unreacted glycerol, any unreacted first acid, and any unreacted second acid.

30. The method of claim 29, wherein the first acid, the second acid, or both comprise orthophosphoric acid, phosphorus pentoxide, one or more polyphosphoric acids, one or more metaphosphoric acids, or any combination thereof.

31. The method of claim 29, further comprising:
removing one or more inorganic mineral scales by contacting the one or more inorganic mineral scales with the reacted product;
lowering a freeze point of water by adding the reacted product to the water;
deswelling clay particles, polymer particles, or a combination thereof by contacting the clay particles, polymer particles, or the combination thereof with the reacted product;
introducing the reacted product to a wellbore as a drilling fluid or as a component of a drilling fluid;
removing corrosion from a metal by contacting the corrosion with the reacted product;
reducing a formation of hydrates in a fluid containing one or more hydrate-forming constituents by contacting the fluid with the reacted product; or
demulsifying an emulsion by mixing the emulsion with the reacted product.

32. The method of claim 29, further comprising mixing the reacted product with one or more base compounds to produce a neutralized product having a pH of about 6 to about 8; and
removing one or more inorganic mineral scales by contacting the one or more inorganic mineral scales with the neutralized product;
lowering a freeze point of water by adding the neutralized product to the water;
deswelling clay particles, polymer particles, or a combination thereof by contacting the clay particles, polymer particles, or the combination thereof with the neutralized product;
introducing the neutralized product to a wellbore as a drilling fluid or as a component of a drilling fluid;
removing corrosion from a metal by contacting the corrosion with the neutralized product;
reducing a formation of hydrates in a fluid containing one or more hydrate-forming constituents by contacting the fluid with the neutralized product; or
demulsifying an emulsion by mixing the emulsion with the neutralized product.

* * * * *